United States Patent [19]
Stjernschantz et al.

[11] Patent Number: 5,516,796
[45] Date of Patent: May 14, 1996

[54] THIOPROSTAGLANDINS AND -PROSTAGLANDIN-LIKE COMPOUNDS AND THERAPEUTIC USES THEREOF

[75] Inventors: Johan W. Stjernschantz; Bahram Resul, both of Uppsala, Sweden; Laszlo Z. Bito, New York, N.Y.

[73] Assignee: Kabi Pharmacia AB, Uppsala, Sweden

[21] Appl. No.: 217,515

[22] Filed: Mar. 24, 1994

[51] Int. Cl.$^6$ ............................................. A01K 31/557
[52] U.S. Cl. ..................... 514/530; 560/121; 562/503
[58] Field of Search ........................... 560/121; 514/530

[56] References Cited

U.S. PATENT DOCUMENTS

| | | | |
|---|---|---|---|
| 4,218,366 | 8/1980 | Weiss | 560/121 |
| 4,599,353 | 7/1986 | Bito | 514/530 |
| 4,883,819 | 11/1989 | Bito | 514/573 |
| 5,296,504 | 3/1994 | Stjernschantz | 514/530 |

FOREIGN PATENT DOCUMENTS

| | | | |
|---|---|---|---|
| 88/05042 | 7/1988 | WIPO . | |
| WO90/02553 | 3/1990 | WIPO | A61K 31/557 |
| WO92/02496 | 2/1992 | WIPO | C07C 405/00 |
| 92/20648 | 11/1992 | WIPO . | |

OTHER PUBLICATIONS

Floyd, J. Med. Chem. 23 903 (1980).
Ohno et al., "Effect of glutathione content on cellular uptake and growth inhibitory activity of prostaglandin A$_2$ in L-1210 Cells," *Eicosanoids*, Springer International, §¶vol. 5, No. 1/1992, pp. 81–85 (1992).
Cagen et al., "The Glutathione Conjugate of Prostaglandin A$_1$ is a Better Substrate Than Prostaglandin E for Partially Purified Avian Prostaglandin E 9–Ketoreductase*," *Biochimica et Biophysica Acta*, Elserier/North–Holland Biomedical Press, BBA51245, pp. 547–551 (1979).
Parker et al., "Formation of a Prostaglandin A$_2$–Glutathione Conjugate in L1210 Mouse Leukemia Cells" *Biomedical Pharmacology*, Pergamon Press PLC vol. 43, No. 5, pp. 1053–1060 (1991).
Cagen et al., "Formation of Glutathione Conjugates of Prostaglandin A$_1$ in Human Red Blood Cells" *The Journal of Biological Chemistry*, vol. 251, No. 21, pp. 6550–6554 (1976).
Atsmon et al., "Conjugation of 9–Deoxy–$\Delta^9$, $\Delta^{12}$(E)–prostaglandin D$_2$ with Intracellular Glutathione and Enhancement of Its Antiproliferative Activity by Glutathione Depletion[1]", *Cancer Research*, 50 pp. 1879–1885 (1990).
Honn et al., "Require of a Reactive A,B–Unsaturated Carbonyl for Inhibition of Tumor Growth and Induction of Differentiation by A Series Prostaglandins," *Biochemical and Biophysical Research Communication*, vol. 129, No. 1 pp. 34–40 (1985).
*M. Brawner Floyd, et al., Prostaglandins and Congeners, 22.1 Synthesis of 11–Substituted Derivatives of 11–Deoxyprostaglandins E1 and E2. Potential Bronchodilators, J. Med. Chem. vol. 23, 1980, pp. 903–913, see p. 905.

*Primary Examiner*—Robert Gerstl
*Attorney, Agent, or Firm*—Kenyon & Kenyon

[57] ABSTRACT

Thiosubstituted prostaglandin derivatives and related compounds having the general structure

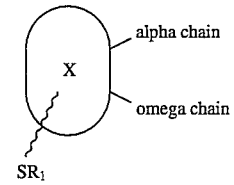

useful as intraocular pressure reducing agents; pharmaceutical compositions containing such compounds; and methods of treatment using such compositions are disclosed.

5 Claims, No Drawings

THIOPROSTAGLANDINS AND -PROSTAGLANDIN-LIKE COMPOUNDS AND THERAPEUTIC USES THEREOF

FIELD OF THE INVENTION

The present invention is related to thiosubstituted derivatives of prostaglandins and related compounds, their synthesis and therapeutic use, especially as intraocular pressure (IOP) reducing agents.

BACKGROUND OF THE INVENTION

Naturally occurring prostaglandins and certain derivatives thereof have been suggested for therapeutic use for the management of cardiovascular, gastro-intestinal, renal, pulmonary, dermatologic, ocular, genital and reproductive conditions. However, because of the side effects of natural prostaglandins and also of their more selective currently available derivatives or analogues, most of the therapeutic potential of such compounds has not yet been realized. This is quite evident from the fact that only a very limited number of prostaglandin-based pharmaceuticals have been made available to the market, in spite of the extensive literature and number of patents and patent applications suggesting their use.

Prostaglandins are a group of naturally occurring compounds derived from unsaturated 20-carbon fatty acids. Virtually all tissues of the body produce prostaglandins and other eicosanoids. The prostaglandins have a variety of important physiologic functions and are classified as autacoids or "local hormones".

The basic chemical structure of naturally occurring prostaglandins is illustrated below:

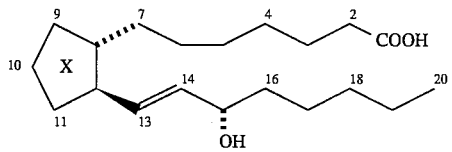

Prostaglandins generally consist of a cyclopentane ring, denoted "X" in the above formula, and two side chains. The upper side chain or "alpha chain" contains 7 carbon atoms. The lower side chain or "omega chain" contains 8 carbon atoms. The end of the alpha chain is normally a carboxylic acid moiety, as indicated above. The side chains may contain 1 to 3 double bonds, most frequently 2, the double bonds being situated between carbon atoms 5 and 6 on the alpha chain and between atoms 13 and 14 on the omega chain. The double bond on the alpha chain exhibits cis-configuration, whereas the double bond on the omega chain exhibits trans-configuration. A substituent group on carbon 15 in the omega chain is preferred for maximal biological activity. In naturally occurring prostaglandins this substituent is hydroxyl, as indicated above. The configuration and functionalities of the cyclopentane ring (X) is important for selectivity to different prostaglandin receptors and the various configurations are those depicted below:

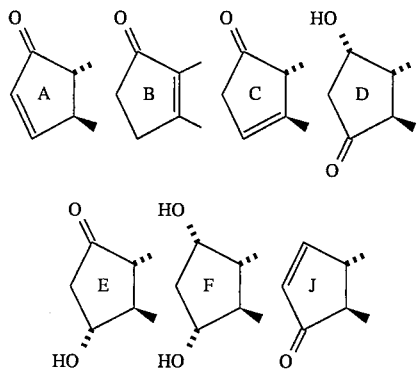

Different classes of prostaglandins are identified by suffixes A, B, C, D, E, P or J depending on the functionalities of the five membered ring, that is the configuration and substituents of the cyclopentane ring. Prostaglandins A, B and C probably are not naturally occurring but rather artificial prostaglandins. Nevertheless they exert considerable biologic activity.

In order to enhance delivery and to improve chemical stability of prostaglandins the carboxylic acid moiety on the alpha chain can be esterified, for instance with hydrocarbon groups containing 1–10 carbon atoms, especially 1–6 carbons, e.g. methyl, ethyl, propyl, isopropyl, butyl, isobutyl, neopentyl or benzyl. Such esterified prodrugs of prostaglandins have been described in several patents and patent applications related to ophthalmic use (see for example, U.S. Pat. No. 4,599,353, U.S. Pat. No. 5,296,504 and W092/02496). Depending on the specific prostaglandin analogue, other derivatives with increased hydrophilicity, such as amides and salts, e.g. the sodium salt, may also be employed.

Glutathione-prostaglandin conjugates and related compounds have been reported in the literature relating to the cytotoxicity of PGA and PGD, see e.g. Cagen, Fales and Pisano, J. Biological Chemistry 251, 6550–54 (1976); Cagen and Pisano, Biochimica et Biophysica Acta 573, 547–51 (1979); Honn and Marnett, Biochemical and Biophysical Research Comn. 129, 34–40 (1985); Atsmon et al., Cancer Res. 50, 1879–85 (1990); Parker and Ankel, Biochemical Pharmacology 43, 1053–60 (1992); Ohno, et al., Eicosanoids 5 81–85 (1992). However, the biological effects of these compounds, other than cytotoxicity or the lack thereof, have not been reported.

SUMMARY OF THE INVENTION

For some time this art has been surveyed to identify prostaglandin analogues which maximally lower intraocular pressure, while minimally causing undesirable side effects such as ocular irritation. As disclosed in U.S. Pat. No. 5,296,504, structurally modified derivatives of natural prostaglandins such as $PGF_{2\alpha}$ and $PGE_2$ with modified omega chains have been identified with these properties.

We have now found that compounds of the class of thioprostaglandins or thioprostaglandin-type compounds with the general structure:

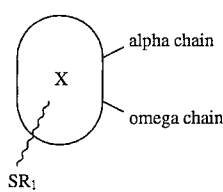

exhibit such beneficial characteristics.

The ring X in the general structure above is a five to seven-membered ring containing an sulfur-containing substituent. Preferably X contains at least one keto or hydroxyl functional group. Examples of suitable ring structures include:

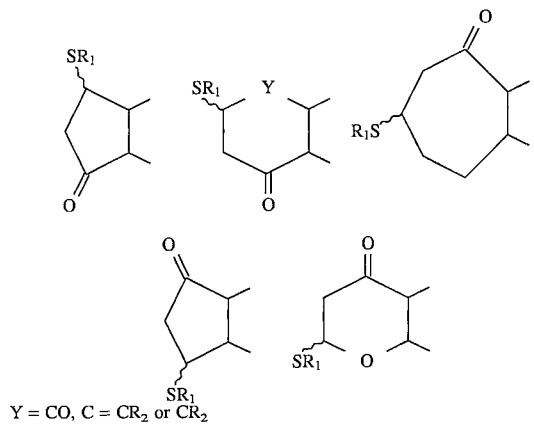

Y = CO, C = CR₂ or CR₂ in which R is hydrogen or alkyl, and in which R, is:

(a) a straight or branched alkyl or alkene chain, preferably with 1–10 carbon atoms in the chain, more preferably 1–5 atoms, optionally interrupted by or incorporating one or more heteroatoms (O, S or N), which may incorporate or be substituted with a ring structure selected from the group consisting of
  (i) cycloalkyl or cycloalkenyl groups with 3–7 carbon atoms in the ring, preferably with 5 or 6 carbon atoms in the ring,
  (ii) heteroatom substituted cycloalkyl or cycloalknyl groups with 3–7 atoms in the ring, including, for example, azetidinyl, thiolanyl, piperazinyl, oxazinyl, azepinyl, oxaxepinyl, thiazepinyl or
  (iii) aryl or heteroaryl groups, including, for example, phenyl, phenoxy, thiazyl, imidazoyl, pyrrolidinyl, thiophenyl and oxazolyl,
  each optionally substituted with lower alkyl groups with 1–5 carbon atoms, $C_1$–$C_3$ aliphatic acylamino groups, nitro groups, halogen atoms and aryl groups, or
(b) an amino acid residue, derived from, for example, cystine or methionine, or
(c) a polypeptide residue containing 2–10, preferably 2–3 amino acids and containing at least one SH moiety.

The ring X may also contain additional substituents. However, it is preferred that such substituents do not adversely affect the affinity for the receptor to be affected by a given compound, the ease of synthesis of the thioprostaglandin, the yield or purity of the product. Examples of suitable additional ring substituents are inert groups like lower alkyl groups, for instance methyl or ethyl.

Preferred embodiments of the invention include therapeutically active 11-thioprostaglandins of type A or 9-thioprostaglandins of type J, or derivatives thereof.

Examples of substances prepared according to the present invention are shown in Table I.

TABLE I

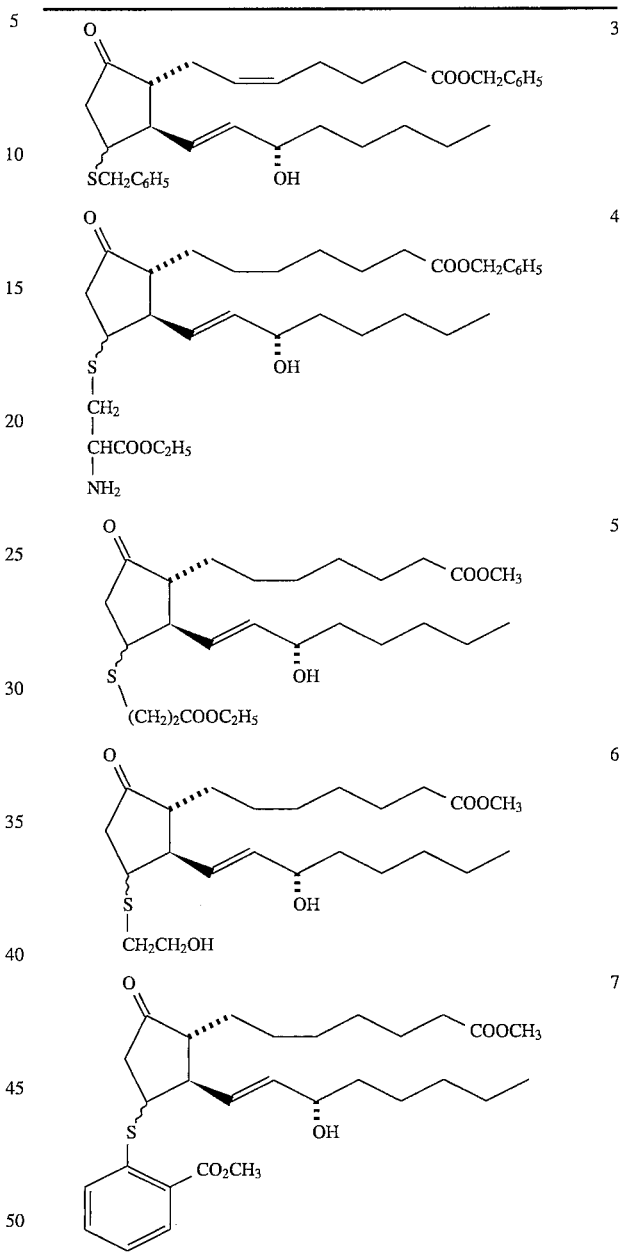

These compounds include methyl and benzyl esters of PGA and PGJ in which $R_1$ is $CH_2C_6H_5$ (3), $CH_2$—$CH(COOC_2H_5)$—$NH_2$ (4), $(CH_2)_2COOC_2H_5$ (5), $CH_2CH_2OH$ (6), and o—$C_6H_4COOCH_3$ (7).

The omega and alpha chains may be the naturally occurring side chains as illustrated above, or may be substituted with various substituents such as alkyl or aryl groups, preferably lower alkyl groups with 1–5, more preferably 1–3 atoms, oxo, hydroxyl or hydroxyalkyl with 1–5, or preferably 1–3 carbon atoms. Preferably there are not more than three oxo or hydroxyl groups in each side chain.

Patent application WO90/02553 discloses methods for introducing a ring structure into the omega chain of prostaglandins with little or no side reaction. The thioprostaglandins of one embodiment of the present invention contain such a ring structure. These ring structures comprise aryl or heteroaryl rings, e.g. phenyl, thiazyl, imidazolyl, pyrrolidinyl, thiophenyl and oxazolyl; cycloalkyl or cycloalkenyl with 3–7 atoms in the ring, preferably 5 or 6 atoms in the ring; or other ring structures having 3–7 atoms in the ring and containing one or more heteroatoms, such as azetidinyl, thiolanyl, piperazinyl, oxazinyl, azepinyl, oxaxepinyl, thiazepinyl, any of which may be substituted with halogen, lower alkyl, lower alkoxy, and so forth. The 17-phenyl prostaglandins are of particular benefit, and especially the 17-phenyl-18,19,20-trinor prostaglandins.

Compounds of the present invention can be synthesized by reacting a prostaglandin or -prostaglandin-like compound with a ring X containing an alpha, beta unsaturated ketone with a sulfhydryl compound $HS-R_1$. By such reaction, thiosubstitutents can be introduced β to a suitably situated carbonyl group, which may then be partially reduced to an alcohol functionality or completely reduced to a methylene ($-CH_2-$) group. Other methods of introducing thiosubstituents, and of modifying the resulting array of functional groups are known in the art.

Suitable cyclic ketones include

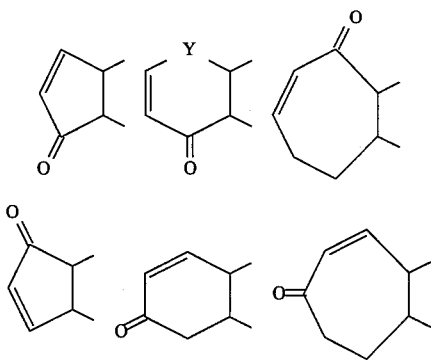

in which Y is defined as above.

A and J type Prostaglandins are of particular interest, since the cyclopentyl ring contains an α,β unsaturated ketone that can be used for coupling of the sulphur-containing substituent.

One aspect of our invention is a composition for treating glaucoma or ocular hypertension containing one of the thioprostaglandin or -prostaglandin-type compounds of this invention. Such a composition contains an effective amount of such a thiosubstituted compound, for example, about 0.1–30 μg, especially 1–10 μg, per application of the active substance, i.e., a therapeutically active and physiologically acceptable derivative from the group defined above. The prostaglandin derivative is mixed with an ophthalmologically compatible vehicle commonly known and used in the art. The vehicle which may be employed for preparing compositions of this invention comprises aqueous solutions as e.g., physiological salines, oil solutions or ointments. The vehicle furthermore may contain ophthalmologically compatible preservatives such as benzalkonium chloride, surfactants such as polysorbate 80, liposomes or polymers, for example, methyl cellulose, polyvinyl alcohol, polyvinyl pyrrolidone and hyaluronic acid, which may be used for increasing the viscosity of the composition. Soluble or insoluble drug inserts may also be employed.

Another aspect of our invention is a method for treating glaucoma or ocular hypertension by contacting an effective intraocular pressure reducing amount of a composition containing one of the thioprostaglandin or -prostaglandin-type compounds of this invention, with the eye, in order to reduce the eye pressure and to maintain said pressure at a reduced level. Such a treatment may advantageously be carried out in that one drop of the composition, corresponding to about 30 μL, is administered about 1 to 2 times per day to the patient's eye. This therapy is applicable both to human beings and to animals.

In vitro bioassay studies of thioprostaglandins according to this invention have shown that such thioprostaglandins exert biological effects on several mammalian tissues and organ systems. Thus, for example, 11-deoxy-11-[ thio(2-amino-1-ethylpropionate)]-$PGE_2$ benzyl ester (4) and 11 deoxy-11-thiobenzyl-$PGE_2$ benzyl ester (3) were found to stimulate the rat gastric fundus, cat iris sphincter, bovine iris sphincter, and the circular (but not the longitudinal) preparation of the guinea pig ileum, and to affect platelet aggregation. These biological effects have no known relationship to the IOP lowering effects of these prostaglandins. These observations demonstrate that thioprostaglandins must be regarded as a new class of drugs that can be used for the therapeutic manipulation of various organ systems, such as the gastrointestinal and cardiovascular systems.

DETAILED DESCRIPTION OF PREFERRED EMBODIMENTS

EXAMPLES

Synthesis of prostaglandin derivatives $PGA_2$ methyl ester 1 and $PGA_2$ benzyl ester 2 are prepared as shown in Scheme 1. The commercially available compound $PGA_2$ is esterified in acetone with isopropyl iodide in the present of N-ethyl diisopropyl amine. The product was then chromatographed on silica gel, using ethyl acetate as eluent.

Scheme I

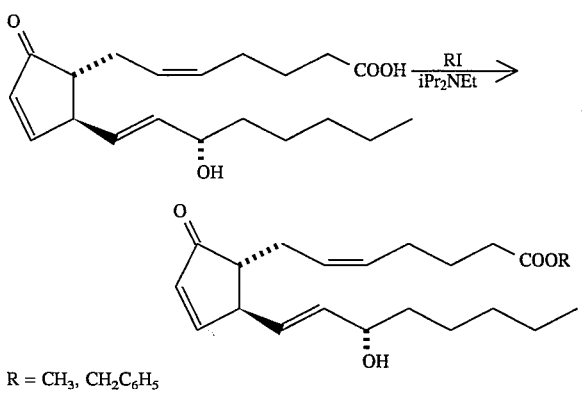

$R = CH_3, CH_2C_6H_5$

PGA adducts 3–7 (Table I) were prepared as shown in Scheme 2. PGA ester was reacted with alkyl mercaptan in methanol or acetonitrile in the presence of a catalytic amount of potassium carbonate.

Scheme II

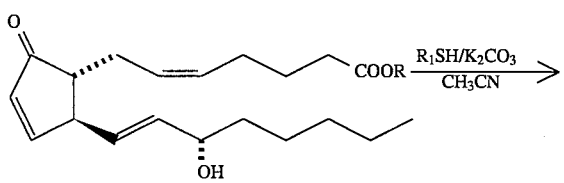

-continued
Scheme II

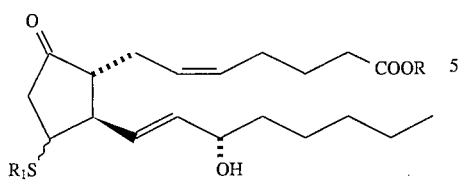

PGA$_2$ methyl ester (1)

To a solution of PGA$_2$ (100 mg, 0.30 mmol) in acetonitrile (5 mL), were added ethyl diisopropyl amine (135 mg, 1.19 mmol) and a methyl iodide (170 mg, 1.19 mmol) in acetonitrile (2 mL). The reaction mixture was warmed to 45°–50° C. for 3–4 hours (TLC monitoring). The solution was diluted with diethyl ether (30 mL) and washed with water (20 mL). The water layer was extracted with diethyl ether (30 mL). The combined organic layer was washed with brine (2×10 mL) and citric acid 5% (2×10 mL). The organic phase was then dried on magnesium sulfate, and filtered. The solvent was removed in vacuo to give a colorless oil, which was purified by column chromatography on silica gel using diethyl ether:ethyl acetate 3:1 as eluent, to yield a colorless oil: yield 65 mg (63%). 1H NMR (CDCl$_3$) d 0.9 (3H CH$_3$), 1.25 (m, 6H), 1.45 (m, 2H), 1.65 (pent, 2H), 2.05–2.2 (m, 3H), 2.22–2.26 (m, 3H) 2.46 (m, 1H), 3.6 (s, 3H), 4.5 (q, 1H), 5.4 (m, 2H); 5.6 (m, 2H); 6.2 (d, 1H); 7.45 (d, 1H).

PGA$_2$ benzyl ester (2)

N-ethyl diisopropyl amine (60 mg, 0.897 mmol) was added dropwise to a stirred solution of PGA$_2$ (60 mg, 0,179 mmol) in CH$_3$CN (5 mL) at 0° C. The mixture was allowed to warm to room temperature whereupon benzyl bromide (171 mg, 0,897 mmol), was added dropwise. After being stirred from 20 hr. (TLC monitoring), the mixture was diluted with ether (50 mL), then washed with brine (20 mL) and citric acid 3% (30 mL). After drying with anhydrous sodium sulfate the solvent was removed in vacuo. The residual oil was chromatographed on silica gel using ether as eluent. This afforded 56 mg (74%) of the title compound as a colorless oil. R$_f$=0.62 (EtOAc) $^1$H NMR (CDCl$_3$) d 0.9 (3H CH$_3$), 1.25 (m, 6H), 1.45 (m, 2H), 1.65 (pent, 2H), 2.05–2.2 (m, 3H), 2.20–2.40 (m, 3H), 2.46 (m, 1H), 4.1 (q, 1H), 5.1 (s, 2H), 5.4 (m, 2H); 5.6 (m, 2H); 6.2 (d, 1H); 7.25 (m, 5H); 7.55 (d, 1H).

The esters of methyl and benzyl esters of 17-phenyl-18,19,20-trinor-PGE$_2$ (compounds 8 and 9) can be similarly prepared from the commercially available 17-phenyl-18,19,20-trinor-PGE$_2$.

11-deoxy-11-thiobenzyl-PGE$_2$ benzyl ester (3)

To a stirred solution of PGA$_2$ benzyl ester (5 mg, 0.012 mmol) in CH$_3$CN (2 mL) at room temperature were added benzyl mercaptol (3.0 mg, 0.024 mmol), and potassium carbonate (1.8 mg). The reaction mixture was stirred at room temperature for 5 h. The mixture was chromatographed on silica gel using a gradient elution with dichloromethane, dichloromethane: ethyl acetate 5:1. This afforded a colorless oil: yield 5.7 mg (89%) R$_f$=0.73 (EtOAc:CH$_2$Cl$_2$ 1:1) $^1$H NMR (CDCl$_3$) d 0.9 (3H CH$_3$), 1.25 (m, 6H), 1.45 (m, 2H), 1.65 (m, 2H), 2.1–2.2 (m, 2H), 2.20–2.40 (m, 3H), 2.46 (m, 1H), 2.8 (m, 1H), 4.1 (q, 1H), 5.1 (s,2H); 5.1(s,2H); 5.25 (m, 1H); 5.4 (m, 1H); 7.25 (m, 10H)

11-Deoxy-11-[3-thio-2-amino-1-ethylpropionate)]-PGE$_2$ benzyl ester (4)

This was prepared as compound 3 from PGA$_2$ benzyl ester (20 mg, 0.0471 mmol) and cysteine. The crude product was chromatographed (silica gel EtOAc:Acetone 1:1); yield 22 mg (81%); TLC R$_f$=0.48 (silica gel, acetone: EtOAc 2:1). $^1$H NMR (CDCl$_3$) d 0.9 (3H, CH$_3$), 1.25 (m, 9H), 1.65 (m, 2H), 2.1–2.2 (m, 4H), 2.20–2.40 (m, 6H), 2.9 (m, 2H), 3.6 (t, 2H); 4.2 (m, 2H), 5.1 (s, 2H); 5.25 (m, 1H); 5.4 (m, 1H); 7.25 (m, 5H)

11-Deoxy-11-[3-thio-(1-ethylpropionate)] PGE$_2$methyl ester (5)

This was prepared as compound 3 from PGA$_2$ methyl ester (30 mg, 0.086 mmol), ethyl-3-mercaptopropionate (23.1 mg, 0.172 mmol), and potassium carbonate (5.9 mg, 0.043 mmol). The crude product was chromatographed (silica gel hexane: EtOAc 1:1); yield 17.6 mg (42.9%), $^1$H NMR (CDCl$_3$) d 0.9 (3H CH$_3$), 1.22 (m, 3H), 1.32 (m, 6H), 1.40–1.6 (m, 2H), 1.65 (dp, 2H), 2.05 (m, 2H), 2.12–2.2 (m, 3H), 2.22 (d, 2H), 2.3 (t, 1H), 2.34–2.48 (m, 3H), 2.6 (t, 2H), 2.78–2.96 (m, 2H), 2.98–3.06 (m, 1H), 3.66 (s, 3H), 4.15 (q, 3H), 5.3 (m, 1H); 5.4 (m, 1H), 5.6 (q, 1H); 5.7 (q, 1H);

11-Deoxy-11-(thio-1-ethanol)-PGE$_2$ methyl ester (6)

This was prepared as compound 3 from PGA$_2$ methyl ester (20 mg, 0.0574 mmol), 2-mercaptoethanol (8.97 mg, 0.225 mmol), and potassium carbonate (2.4 mg, 0.017 mmol) in methanol (2 mL). The crude product was chromatographed (silica gel CH$_2$Cl$_2$:EtOAc 1:1); yield 21.8 mg (81%), 1H NMR (CDCl$_3$) d 0.9 (3H CH$_3$), 1.22 (m, 6H), 1.6 (m, 2H), 1.65 (dp, 2H), 2.05 (q, 2H), 2.2 (m, 3H), 2.34 (q, 2H), 2.4–2.5 (m, 3H), 2.9 (m, 4H), 3.06 (m, 1H), 3.66 (s, 3H), 3.8 (m, 3H), 4.2 (q, 1H); 5.3 (m, 1H); 5.4 (m, 1H), 5.6 (q, 1H); 5.7 (q, 1H);

11-Deoxy-11-[thio-2-(methylbenzoate)-]PGE$_2$ methyl ester (7)

This was prepared as compound 3 from PGA$_2$ methyl ester (30 mg, 0.086 mmol), methyl 2-mercaptobenzoate (22 mg, 0.129 mmol), and potassium carbonate (3.6 mg, 0.026 mmol). The crude product was chromatographed using gradient elution with dichloromethane, 5%–10% EtOAc in dichloromethane (silica gel); yield 23.8 mg (54%), 1H NMR (CDCl$_3$) d 0.9 (3H CH$_3$), 1.22 (m, 6H), 1.4 (m, 2H), 2.05 (q, 2H), 2.2 (m, 3H), 2.34 (q, 2H) 2.4 (m, 2H), 2.6 (m, 1H), 3.06 (dd, 1H), 3.66 (s, 3H), 3.9 (s, 3H), 4.1 (m, 1H), 5.3 (m, 1H); 5.4 (m, 1H), 5.6 (q, 1H); 5.7 (q, 1H), 7.2–7.45 (m, 3H), 7.85 (m, 1H).

Similarly, 11-deoxy-11-thiobenzyl-17-phenyl-18,19,20-trinor-PGE$_2$ benzyl ester, 11-Deoxy-11-[3-thio-(2-amino-1-ethylpropionate)]- 17-phenyl-18,19,20-trinor-PGE$_2$ benzyl ester, 11-Deoxy-11-[3-thio-(1-ethylpropionate)]-17-phenyl-18,19,20-trinor-PGE $_2$methyl ester, 11-Deoxy-11-(thio-1-ethanol)-17phenyl, 18-19,20-trinor-PGE2 methyl ester, 11-Deoxy-11-[thio-2-(methylbenzoate)]- 17-phenyl-18,19,20-trinor-PGE$_2$ methyl ester can be prepared from the 17-phenyl-18,19,20-trinor-PGE$_2$ esters 8 and 9.

Studies on the intraocular pressure lowering effect and adverse reactions of thioprostaglandin compounds of the present invention Experiments were performed in cats and rabbits. The test compounds were administered topically to the eye. The compounds were tested by using a single dose of each concentration. The intraocular pressure in cats was measured with a pneumotonometer (Digilab Modular One, Bio-Rad). Before the measurement the cornea was anaesthetized with 1–2 drops of oxibuprocain. The ocular irritation (discomfort) caused by the test compounds was assessed without anaesthesia in the same animals. The irritation was graded on an arbitrary scale 0–3, 0 indicating absence of irritation, and 3 indicating maximum irritation as obvious from complete lid closure. Surface hyperemia of the eye (redness of the eye) was evaluated in rabbits. The eye was photographed at regular intervals and the degree of hyperemia was evaluated from the color photographs in a masked way. The hyperemia was evaluated on an arbitrary scale 0–5, 0 indicating absence of hyperemia and 5 marked hyperemia and conjunctival chemosis. All compounds were formulated in physiologic saline using polysorbate 80 as solubilizer. The same volume of the vehicle only was applied topically on the contralateral control eye.

Data relating to the maximum intraocular pressure reducing effect of compounds 3(11-deoxy-11-thiobenzyl-$PGE_2$-benzyl ester), 4 (11-deoxy-11-[3-thio(-2-amino-1-ethylpropionate)]-$PGE_2$-benzyl ester), 5 (11-deoxy-11-[3-thio-(1-ethylpropionate)]-$PGE_2$-methyl ester), 6(11-deoxy-11-(thio-1-ethanol)-$PGE_2$-methyl ester), and 7 (11-deoxy-11-[thio-(2-methylbenzoate)]-$PGE_2$-methyl ester) are presented in Table II.

TABLE II

Maximum reduction of intraocular pressure in cats 1–3 hours after topical application of different thioprostaglandin compounds (Mean ± SEM; n = 6).

| Comp. no | Dose (ug) | Exp Eye (mmHg) | Cont Eye (mmHg) | Difference (mmHg) | P-value |
|---|---|---|---|---|---|
| 3 | 3 | 14.7 ± −0.7 | 18.3 ± −1.9 | −3.7 ± −1.3 | <0.05 |
| 3 | 5 | 13.0 ± −0.4 | 16.8 ± −0.7 | −3.8 ± −0.5 | <0.001 |
| 4 | 3 | 16.3 ± −0.7 | 20.7 ± −2.0 | −4.3 ± −1.6 | <0.05 |
| 4 | 10 | 14.0 ± −0.7 | 19.8 ± −0.9 | −5.8 ± −1.1 | <0.005 |
| 5 | 1 | 12.7 ± −1.0 | 22.2 ± −1.2 | −9.5 ± −0.8 | <0.001 |
| 5 | 3 | 11.5 ± −1.6 | 20.7 ± −2.6 | −9.2 ± −1.2 | <0.001 |
| 5 | 10 | 12.3 ± −1.3 | 22.3 ± −1.3 | −10.0 ± −0.9 | <0.001 |
| 6 | 1 | 14.7 ± −1.0 | 20.5 ± −1.5 | −5.8 ± −1.0 | <0.005 |
| 6 | 3 | 13.8 ± −0.9 | 19.8 ± −1.5 | −6.0 ± −1.3 | <0.01 |
| 7 | 1 | 16.2 ± −1.3 | 20.5 ± −1.5 | −4.3 ± −0.7 | <0.01 |

As can be seen from these data, all compounds reduced the intraocular pressure by a statistically significantly amount. Except for compound 3, all compounds caused 24 hour reduction of the intraocular pressure. The strongest effect of compounds 3 through 7 was achieved with compound 5 which markedly reduced the pressure at the low dose of 1 μg.

The maximum ocular irritation caused by the different test compounds is presented in Table III.

TABLE III

Maximum ocular irritation after topical application of different thioprostaglandin compounds in cats. The values represent the difference between the experimental and contralateral control eyes (Mean ± SEM, n = 6).

| Comp. no | Dose (μg) | Difference | P-value |
|---|---|---|---|
| 3 | 3 | 0.08 ± −0.08 | >0.05 |
| 3 | 5 | 1.33 ± −0.1 | <0.001 |
| 4 | 3 | 0.75 ± −0.1 | <0.001 |
| 4 | 10 | 0.58 ± −0.08 | <0.001 |
| 5 | 1 | 1.08 ± −0.2 | <0.005 |
| 5 | 3 | 0.58 ± −0.08 | <0.001 |
| 5 | 10 | 2.00 ± −0.1 | <0.001 |
| 6 | 1 | 0.92 ± −0.08 | <0.001 |
| 6 | 3 | 0.67 ± −0.1 | <0.005 |
| 7 | 1 | 1.08 ± −0.2 | <0.005 |

For comparison it should be noted that in the same test system 1 μg of $PGF_{2\alpha}$-isopropyl ester or $PGE_2$-isopropyl ester induces maximum irritation (i.e., grade 3). As can be seen in Table III most compounds caused only mild irritation, when used in doses which reduced the intraocular pressure effectively.

The maximum ocular surface hyperemia caused by the thioprostaglandin compounds tested is presented in Table IV.

TABLE IV

Maximum surface hyperemia of the eye after topical application of different thioprostaglandins in rabbits. (Mean ± SEM, n = 6).

| Comp. no | Dose (μg) | Exp Eye | Cont Eye | Difference | P-value |
|---|---|---|---|---|---|
| 5 | 0.5 | 1.1 ± −0.2 | 0.8 ± −0.2 | 0.3 ± −0.2 | >0.05 |
| 6 | 0.5 | 1.7 ± −0.1 | 0.8 ± −0.2 | 0.8 ± −0.1 | <0.001 |
| 7 | 0.5 | 1.2 ± −0.2 | 0.6 ± −0.1 | 0.6 ± −0.2 | <0.05 |

As can be seen the compounds caused very mild hyperemia in rabbits when used in doses which reduced the intraocular pressure potently in cats. For comparison it should be noted that, e.g., 0.5 μg of $PGF_{2\alpha}$-isopropyl ester or $PGE_2$-isopropyl ester induces ocular surface hyperemia of grade 2.9 or more in the same test system.

Accordingly, the thioprostaglandin compounds of the present invention effectively reduce the intraocular pressure and at dose levels necessary for intraocular pressure reduction exert no or only mild side effects. Thus, thioprostaglandin compounds of the present invention may be used clinically in the treatment of glaucoma or ocular hypertension in humans as well as animals.

We claim:

1. A thioprostaglandin compound which is an 11-deoxy-11-[3-thio-(1-ethylpropionate)]- 17-phenyl-18, 19, 20, trinor-$PGE_2$ methyl ester.

2. A topical pharmaceutical composition for reducing intraocular pressure comprising the compound of claim 1 in an amount sufficient to reduce intraocular pressure, and a pharmaceutically acceptable excipient.

3. A method for reducing intraocular pressure, said method comprising applying the pharmaceutical composition of claim 2 to the eye of a mammalian subject.

4. A topical pharmaceutical composition for reducing intraocular pressure comprising 11-deoxy- 11-[3-thio-1-ethylpropionate]-$PGE_2$-methyl ester in an amount sufficient to reduce intraocular pressure, and a pharmaceutically acceptable excipient.

5. A method for reducing intraocular pressure, said method comprising applying a pharmaceutical composition of claim 4 to the eye of a mammalian subject.

* * * * *